United States Patent [19]

Schack et al.

[11] Patent Number: 4,675,088

[45] Date of Patent: Jun. 23, 1987

[54] SYNTHESIS OF $R_fOTEF_5$

[75] Inventors: Carl J. Schack, Chatsworth; Karl O. Christe, Calabasas, both of Calif.

[73] Assignee: The United States of America as represented by the Secretary of the Air Force, Washington, D.C.

[21] Appl. No.: 824,822

[22] Filed: Jan. 31, 1986

[51] Int. Cl.$^4$ .................. B01J 19/12; C07C 165/00; C01B 7/24
[52] U.S. Cl. .................. 204/157.94; 204/158.11; 204/158.12; 260/550; 423/466; 423/508; 570/123; 570/137
[58] Field of Search ............. 260/550; 568/604, 683, 568/684; 423/466, 508; 570/123, 137; 204/157.94, 158.11, 158.12

[56] References Cited

U.S. PATENT DOCUMENTS 4,462,975  7/1984  Schack et al. .................. 423/473
4,508,662  4/1985  Schack et al. .................. 260/550
4,578,225  3/1986  Schack et al. .................. 260/550

OTHER PUBLICATIONS

C. Schack et al, J. of Fluorine Chemistry, vol. 26(1), pp. 19-28 (1984); vol. 27(1), pp. 53-60 (1984); vol. 24(4), pp. 467-476 (1984).

D. Naumann, W. Habel, P. Reinelt, E. Renk, "Ligandenaustauschreaktionen an Perfluoroorganohalogen-Verbindungen" Forschungsberichte des Landes Nordrhein-Westfalen, Nr. 3115, (1982).

Primary Examiner—Mary E. Ceperley
Attorney, Agent, or Firm—Charles E. Bricker; Donald J. Singer

[57] ABSTRACT

Pentafluorotellurium hypohalites are reacted with fluorocarbon iodides to form intermediate adducts which are thereafter decomposed to form fluorocarbons containing the $TeF_5O-$ group.

12 Claims, No Drawings

SYNTHESIS OF $R_fOTeF_5$

STATEMENT OF GOVERMENT INTEREST

The invention described herein may be manufactured and used by or for the Government of the United States for all governmental purposes without the payment of any royalty.

BACKGROUND OF THE INVENTION

This invention relates to a method for synthesizing fluorocarbon fluids containing an oxypentafluorotellurium group ($-OTeF_5$).

The $TeF_5O-$ group is inherently dense and when incorporated into fluorocarbon fluids it provides enhanced density to those materials. Additionally, the ether-like oxygen link furnishes molecular flexibility, lessening of steric hindrances, and retention of fluid properties.

Fluorocarbon fluids containing the $-OTeF_5$ group find particular utility as agents for a wide variety of applications requiring high density fluids. They are especially useful as flotation agents for gyroscopes, compasses and like instruments which must be dampened to minimize excessive vibration and oscillation problems.

In our U.S. Pat. No. 4,508,662, issued Apr. 2, 1985 to C. J. Schack and K. O. Christe, we disclose the reaction of pentafluorotellurium hypochlorite with olefinic reactants to form fluorocarbon adducts containing the $-OTeF_5$ group. In our pending U.S. patent application Ser. No. 617,456, filed May 29, 1984, we disclose the reaction of xenon bis-pentafluorotellurium oxide with olefinic reactants to form fluorocarbon adducts containing multiple $-OTeF_5$ groups.

It is an object of the present invention to provide a novel process for forming fluorocarbon adducts containing the $-OTeF_5$ group.

Other objects and advantages of the present invention will become apparent upon consideration of the following detailed description.

SUMMARY OF THE INVENTION

In accordance with the present invention there is provided a novel process for producing fluorocarbon compounds containing the $-OTeF_5$ group which comprises the steps of reacting a fluorocarbon iodide containing 1 to 5 carbon atoms with a pentafluorotellurium hypohalite to form an intermediate adduct, and decomposing the intermediate to provide the desired compounds.

The reactions for synthesizing the desired fluorocarbon fluids in accordance with the invention are illustrated by the following equations:

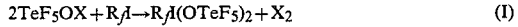

$$2TeF_5OX + R_fI \rightarrow R_fI(OTeF_5)_2 + X_2 \quad (I)$$

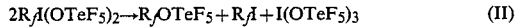

$$2R_fI(OTeF_5)_2 \rightarrow R_fOTeF_5 + R_fI + I(OTeF_5)_3 \quad (II)$$

wherein X is $-Cl$ or $-F$ and $R_f$ is a fluorinated hydrocarbon group of the general formula $-C_mF_nY_p$ wherein Y is $-H$, $-F$, $-Cl$ or $-Br$ and wherein m is an integer between 1 and 5, p is an integer having a value of about $2m/3$ (rounded to the next higher or lower value) and n is an integer having a value of $2m+1-p$. Examples of suitable fluorocarbon iodides include $CF_3I$, $HCF_2CF_2I$, $CF_3CF_2I$, $ClCF_2CF_2I$, $BrCF_2CF_2I$, $HCF_2CF_2CF_2I$, $CH_3CHFCF_2I$, $ClCF_2CF_2CF_2I$, $CF_3CFBrCF_2I$, $C_4F_9I$, $C_4HF_8I$, $C_4ClF_8I$, $C_4BrF_8I$ and cyclo-$C_5F_9I$.

The pentafluoroetellurium hypohalites can be prepared following the procedures given in U.S. Pat. No. 4,508,662. The fluorocarbon iodides are commercially available from, for example, PCR, Inc., Gainesville, FL, and Columbia Organics, Camden, S.C.

The reaction (I) between the pentafluorotellurium hypohalite and fluorocarbon iodide is initiated at subambient temperatures. The hypohalite reactant and the fluorinated hydrocarbon reactant are cocondensed at subambient temperature and allowed to gradually warm toward ambient temperature. The progress of the reaction may be monitored by removing and measuring the evolved halogen gas or other products volatile at the reduced temperature.

Decomposition of the adduct formed by the reaction I is accomplished by heating the adduct or by exposure to UV radiation or a combination thereof.

The conditions of reaction (I) and decomposition (II) will vary depending upon the reactants employed. In the case of the methyl adduct, the reaction (I) is carried out at or below about $-78°$ C. for about 10 to 100 hours. In the case of the $C_2$ to $C_5$ reactants, the reaction (I) mixture is cocondensed at a temperature sufficiently low to ensure condensation of both reactants. Liquid nitrogen may be employed for this step. The reactor containing the condensed reactants is then closed and thereafter allowed to slowly warm to, for example, about $-78°$ C. in a liquid nitrogen $-CO_2$ slush bath. The reaction mixture may be held at $-78°$ C. for 0.1 to 10 hours, then warmed slowly to ambient temperature. Except for the methyl adduct, the reaction mixture is maintained at ambient temperature for about 10 to 60 hours and then the resulting reaction products are separated by removing the volatile material. Decomposition of the methyl adduct is accomplished by warming the material above $-78°$ C.

The final product $R_fOTeF_5$ is obtained by decomposition of the above adducts. Decomposition of the ethyl and higher alkyl adducts is accomplished by heating the $R_fI(OTeF_5)_2$ material to at least about $100°$ C., preferably about $115°-120°$ C. for about 1 to 10 hours. Alternatively, the $R_fI(OTeF_5)_2$ material can be photolytically decomposed using UV radiation of sufficient intensity to accomplish the desired decomposition in a reasonable time.

In the examples which follow, volatile materials were manipulated in a stainless steel vacuum line equipped with Teflon FEP U-traps, 316 stainless steel bellows-seal valves, and a Heise Bourdon tube-type gauge. The synthetic reactions employed here were usually conducted in stainless steel cylinders. Infrared spectra were recorded on a Perkin Elmer Model 283 spectrophotometer using cells equipped with AgBr windows. Raman spectra were recorded at ambient temperature on a Cary Model 83 spectrophotometer with the use of the 488 Å exciting line of an Ar ion laser. To avoid decomposition, the Raman spectrum of the yellow solid, $I(OTeF_5)_3$, was recorded at $-140°$ C. on a Spex Model 1403 spectrophotometer using the 6471 Å exciting line of a Kr ion laser and a premonochromator for the elimination of plasma lines. Sealed quartz tubes, 3 mm OD, or Pyrex mp capillaries were used as sample containers. $^{19}F$ nmr spectra were recorded at 84.6 MHz on a Varian Model EM390 spectrometer with internal $CFCl_3$ as a standard with negative chemical shifts being upfield from $CFCl_3$.

The following examples illustrates the invention:

EXAMPLE $2TeF_5OCl + R_fI \rightarrow R_fI(OTeF_5)_2$, General Procedure

A tared cylinder was cooled to $-196°$ C. and measured quantities of $R_fI$ and $TeF_5OCl$ were successively condensed in. The closed cylinder was placed in a dewar containing a liquid N2-dry ice slush and this was allowed to warm slowly from $-196°$ to $-78°$ C. in a dry ice chest. Monitoring the progress of the reaction at $-78°$ C. was accomplished by removing and measuring the evolved $Cl_2$ or other products volatile at $-78°$ C. After a period at $-78°$ C. the reaction mixtures were warmed slowly to ambient temperature to complete the oxidative addition reaction. For $CF_3I$ the resulting adduct was unstable and decomposed above $-78°$ C. to give $CF_3OTeF_5$ (trapped at $-126°$ C. on fractionation) and other products. For the other fluorocarbon iodides, after removal of all volatile materials at room temperature, there remained in the cylinders the colorless addition compounds of compositions, $R_fI(OTeF_5)_2$. These were low melting solids, $C_2F_5I(OTeF_5)_2$, $30°-31°$ C. and $n-C_3F_7I(OTeF_5)_2$, $49°-51°$ C., $i-C_3F_7I(OTeF_5)_2$, $16°-17°$ C.

Synthesis data are given in Table I, below:

TABLE I

Synthesis of $R_fI(OTeF_5)_2$

| $R_fI$ (mmol) | $TeF_5OCl$ (mmol) | Temp. Max °C. | Time (days) | Product | Yield, %[a] |
|---|---|---|---|---|---|
| $CF_3I$ (0.91) | 1.85 | $-78$ | 4 | $CF_3I(OTeF_5)_2$ | ~80 |
| $C_2F_5I$ (1.10) | 2.58 | $+25$ | 3 | $C_2F_5I(OTeF_5)_2$ | 95 |
| $n-C_3F_7I$ (2.56) | 5.62 | $+25$ | 2 | $n-C_3F_7I(OTeF_5)_2$ | 94 |
| $i-C_3F_7I$ (2.16) | 4.73 | $+25$ | 2 | $i-C_3F_7I(OTeF_5)_2$ | 97 |

[a]Yield based on the limiting reagent

GENERAL PROCEDURE $2R_fI(OTeF_5)_2 \rightarrow R_fOTeF_5 + R_fI + I(OTeF_5)_3$ In the dry box a tared cylinder was loaded with a weighed amount of the $R_fI(OTeF_5)_2$ compound. The cylinder was then evacuated, closed and placed in an oven at $115°-120°$ C. for several hours. After recooling to ambient temperature, the contents of the reactor were separated by fractional condensation, measured and identified by their infrared and $^{19}F$ nmr spectra. In addition to the $R_fOTeF_5$ product generally obtained (see text), the significant volatile products were $R_fI$ and some $R_fF$. Lesser amounts of the $TeF_6$ and $TeF_5OTeF_5$ were sometimes encountered. Left behind in the cylinder was crude $I(OTeF_5)_3$ identified by infrared and Raman spectroscopy and usually present in 80-90% yield based on the disproportionation reaction shown. For the photolytic decomposition of $R_fI(OTeF_5)_2$, Pyrex reactors were loaded in the dry box, evacuated, and irradiated with a Hanovia 100 W Utility lamp. Along with $I(OTeF_5)_3$ the photolysis products included variable amounts of the coupling product $R_fR_f$, isomers of $C_6F_{14}$, and $C_3F_7I$.

TABLE IIa

Thermal Decomposition of $R_fI(OTeF_5)_2$

| Adduct | Temp, max °C. | Time (hours) | Product | Yield %[a] |
|---|---|---|---|---|
| $CF_3I(OTeF_5)_2$ | 25 | 2 | $CF_3OTeF_5$ | 17 |
| $C_2F_5I(OTeF_5)_2$ | 115 | 21 | $C_2F_5OTeF_5$ | 78 |
| $n-C_3F_7I(OTeF_5)_2$ | 115 | 26 | $n-C_3F_7OTeF_5$ | 30 |
| $i-C_3F_7I(OTeF_5)_2$ | 120 | 10 | (note [b]) | — |

TABLE IIb

UV Decomposition of $R_fI(OTeF_5)_2$

| Adduct | Temp °C. | Time (hours) | Product | Yield %[a] |
|---|---|---|---|---|
| $n-C_3F_7I(OTeF_5)_2$ | 25 | 18 | $n-C_3F_7OTeF_5$ | 77 |
| $i-C_3F_7I(OTeF_5)_2$ | 25 | 16 | (note [b]) | — |

[a]Yield based on the stoichiometry of reaction II
[b]no $R_fOTeF_5$

Identification of the products of the process of this invention as based on spectroscopic properties. Data for $C_2F_5OTeF_5$ and $n-C_3F_7OTeF_5$ were consistent with the literature data for these compounds.

The $^{19}F$ NMR spectrum of $CF_3OTeF_5$ was that expected for an $AB_4$ spin system ($TeF_5O$— possesses one apical and four equatorial fluorines) and an alkyl fluorocarbon. Observed NMR parameters were [ppm(multiplicity)]; where b-broad, d-doublet, t-triplet, and qi-quintet. For $F^A Te_4{}^B OCF_3{}^X$: A-50.2, B-44.3 ($B_4$), X-51.6 (qi); $J_{AB}=190$, $J_{BX}=4.4$. Infrared bands noted were, $cm^{-1}$ (intensity): 1263(s), 1233(s), 1192(s), 743(s), 710(m), and 324(s).

Various modifications and alterations may be made in the present invention without departing from the spirit thereof or the scope of the appended claims.

We claim:

1. A high density $TeF_5O$— substituted, fluorocarbon having the formula $YCF_2OTeF_5$ wherein Y is —H, —F, —Cl or —Br.

2. The compound of claim 1 wherein Y is —F.

3. A process for synthesizing a $TeF_5O$— substituted fluorocarbon having the formula $R_fOTeF_5$ which comprises the steps of:
(a) cocondensing a primary fluorocarbon iodide having the formula $R_fI$ and a pentafluorotellurium hypohalite having the formula $TeF_5OX$ wherein X is —Cl or —F at a subambient temperature;
(b) allowing the resulting mixture of reactants to warm toward the ambient temperature whereby said reactants react to form an intermediate product having the formula $R_fI(OTeF_5)_2$;
(c) applying energy to decompose said intermediate; and
(d) recovering said $TeF_5O$— substituted fluorocarbon;
wherein $R_f$— is a fluorinated hydrocarbon group of the general formula —$C_mF_nY_p$, wherein Y is —H, —F, —Cl or —Br, m is an integer having a value of 1 to 5, p is an integer having a value of about $2m/3$ rounded to the next lower or higher number and n is an integer having a value of $2m+1-p$.

4. The process of claim 3, wherein said fluorocarbon iodide is trifluoromethyl iodide and said hypohalite is selected from the group consisting of pentafluorotellurium hypofluorite and pentafluorotellurium hypochlorite.

5. The process of claim 4 wherein said reacting step is carried out at a temperature between co-condensation temperature of said iodide and said hypohalite reactants and about −78° C. for about 10 to 100 hours and wherein said decomposing step is carried out by warming the material above −78° C.

6. The process of claim 3 wherein said hypohalite is pentafluorotellurium hypochlorite.

7. The process of claim 6 wherein said fluorocarbon iodide is pentafluoroethyl iodide.

8. The process of claim 6 wherein said fluorocarbon iodide is heptafluoro-n-propyl iodide.

9. The process of claim 3 wherein said fluorocarbon iodide has between 2 and 5 carbon atoms and wherein said reacting step is carried out at a temperature between about −78° C. and ambient temperature for about 0.1 to 10 hours and thereafter at ambient temperature for about 10 to 60 hours.

10. The process of claim 9 wherein said decomposing step is carried out by heating said intermediate product to at least about 100° C. for about 1 to 10 hours.

11. The process of claim 10 wherein said intermediate is heated to about 115°–120° C.

12. The process of claim 9 wherein said decomposing step is carried out photolytically.

* * * * *